(12) United States Patent
Bonn et al.

(10) Patent No.: US 8,105,513 B2
(45) Date of Patent: Jan. 31, 2012

(54) PIPETTE TIP CONTAINING PARTICLE-FILLED POLYMER MONOLITH

(76) Inventors: Alexander Bonn, Zirl (AT); Guenther Bonn, Zirl (AT); Christian Huck, Felseckstr. 5 (AT); Bernhard Maerk, Birgitz (AT); Harald Sonderegger, Innsbruck (AT); Mathias Rainer, Grinzens (AT); Douglas T. Gjerde, Saratoga, CA (US)

( * ) Notice: Subject to any disclaimer, the term of this patent is extended or adjusted under 35 U.S.C. 154(b) by 412 days.

(21) Appl. No.: 12/479,676

(22) Filed: Jun. 5, 2009

(65) Prior Publication Data

US 2010/0009845 A1 Jan. 14, 2010

Related U.S. Application Data

(60) Provisional application No. 61/131,204, filed on Jun. 6, 2008.

(51) Int. Cl.
- *B05D 7/22* (2006.01)
- *B01L 3/02* (2006.01)
- *B01D 35/02* (2006.01)

(52) U.S. Cl. ........ 264/112; 422/524; 422/534; 427/235; 427/238

(58) Field of Classification Search .................. None
See application file for complete search history.

(56) References Cited

U.S. PATENT DOCUMENTS

| 6,048,457 | A | 4/2000 | Kopaciewicz et al. | |
|---|---|---|---|---|
| 2006/0115384 | A1 | 6/2006 | Wohleb | |
| 2006/0201881 | A1 | 9/2006 | Marcus et al. | |
| 2007/0065356 | A1 * | 3/2007 | Cabrera et al. | 423/338 |
| 2008/0035558 | A1 | 2/2008 | Shah | |
| 2008/0119637 | A1 * | 5/2008 | Gjerde et al. | 530/334 |

FOREIGN PATENT DOCUMENTS

| WO | WO 98/37949 A1 | 9/1998 |
|---|---|---|
| WO | WO 02/40131 A1 | 5/2002 |
| WO | WO2007/106483 A2 | 9/2007 |

OTHER PUBLICATIONS

Hsieh et al. J. Chromatogr. A 1165 (2007) 128-135. Development of a titanium dioxide nanoparticle pipette-tip for the selective enrichment of phosphorylated peptides.

Hsu et al. Electrophoresis. Nov. 2004;25(21-22):3840-7. Photopolymerized microtips for sample preparation in proteomic analysis.

Kowa Product List.

* cited by examiner

*Primary Examiner* — Mary F Theisen
(74) *Attorney, Agent, or Firm* — Sue S. Kalman

(57) ABSTRACT

The present invention relates to a pipette tip which is fitted with a porous organic monolith which is doped with active particles. Due to a unique polymerization method, the extraction tips stay highly permeable which allows sample to pass through the monolithic bed. The extraction tip represents an ideal tool for solid phase extraction, especially for desalting, isolating and purifying biomolecules such as peptides and proteins.

10 Claims, 7 Drawing Sheets

PIPETTE TIP CONTAINING PARTICLE-FILLED POLYMER MONOLITH

CROSS REFERENCE TO RELATED APPLICATIONS

This application claims priority to and benefit of U.S. Provisional Patent Application No. 61/131,204 filed Jun. 6, 2008, the disclosure of which is incorporated herein by reference in their entirety for all purposes.

FIELD OF THE INVENTION

The present invention relates to a method of producing a pipette tip into which is fitted with a hollow monolith porous polymer structure doped with particles having active functional sites. A center hollow channel is created inside the tip using a unique stable, pre-monolith suspension and polymerization process. During the tip manufacturing process, the stable, pre-monolith suspension is added to the tip, a center hollow space is created without the outer stable, pre-monolith suspension draining from the pipette tip, and then the structure is polymerized. Due to this unique method, the resulting extraction tips are highly permeable allowing the sample to pass easily through the monolithic bed structure. The extraction tip is an ideal tool for solid phase extraction, especially for desalting and for isolating and purifying biomolecules such as peptides, proteins, nucleic acids, carbohydrates, lipids and other biomolecules.

BACKGROUND OF THE INVENTION

The development and utility of new high-throughput methods based on efficient extraction materials for purification and desalting of complex samples is of utmost importance. The complexity of biofluids, especially blood serum containing non-volatile salts, hinders the use of analytical tools. In proteomics and other biological fields, pre-treatment of sample is one of the most important procedures to pre-concentrate low concentrated analytes and to remove suppressing compounds such as salts or detergents before interfacing with mass spectrometry (MS). Compounds, especially at very low concentrations, often get their mass spectrometry signal suppressed by salts and other impurities. Therefore, a prior purification and separation step of biological samples is valuable. Several methods have been reported for sample treatment prior to MS analysis. These include dialysis, ultrafiltration, size-exclusion, affinity purification and solid phase extraction (SPE). Ultrafiltration and size-exclusion spin columns do not provide a sufficient degree of desalting. Dialysis often works well, but is difficult and expensive to automate. SPE is one of the most popular sample preparation methods to handle such problems and is very often used with matrix-assisted laser desorption/ionization (MALDI) MS. SPE with reversed phase (C4, C8 or C18) functional groups is the common strategy to desalt and concentrate protein and peptide samples. Other SPE materials based on hydrophilic interactions such as immobilized metal-ion affinity chromatography (IMAC) or porous graphitic carbon (PGC) have been proposed for purifying those categories of peptides prior to MS. PGC columns are normally used to purify carbohydrates and glycopeptides, but have recently been shown as an alternative or supplement to traditional reversed phase (RP) chromatography for separation of small and hydrophilic peptides prior to MALDI MS analysis.

The analysis of phosphorylated proteins and peptides is highly demanded, since protein phosphorylation is known as the most common post-translational modification found in nearly all cellular processes. Three amino acids, serine, threonine as well as tyrosine are common phosphorylation sites. Enrichment of phosphorylated proteins and peptides is generally required before mass spectrometric analysis because the abundance of phosphorylated forms is frequently low. Among various strategies used in enrichment of phosphorylated species the recently described metal oxide affinity chromatography (MOAC) is considered to be an efficient method. Metal oxides such as titanium dioxide ($TiO_2$) or zirconium dioxide ($ZrO_2$) have been successfully applied to selectively retain phosphopeptides from complex biological mixtures.

U.S. Pat. No. 6,048,457 describes a method for casting-in-place composite and/or non-filled structures which are useful as sorptive or reactive media or for size-based separations. Any particular housing size or configuration can be used, and the inclusion of a large amount of adsorptive particles in polymer is achieved while still maintaining the membrane three dimensional structure. In a first preferred embodiment, the composite structures comprise particles entrapped within a porous polymeric substrate, and are cast in-place into a housing such as a pipette tip, thereby providing an effective platform for micromass handling. However, the casting polymer is very hydrophobic and limits the overall chemistry of the tips.

U.S. Pat. application. 2006/0,115,384 discloses a sorption pipette tip for the extraction of a sample, or analyte, from a sample matrix with a method of using the sorption pipette tip to perform the extraction. The pipette tip has a coating of a sorptive material. The orifice of the tip may have different configurations that enhance extraction.

Pat. No. WO 02/40131 reveals a device for small volume sample preparation using tubes columns, and sheets, such as capillaries or pipette tips, in which particles of a separation medium, such as particles of a chromatography material used for sample preparation, are directly embedded in the solid material composing the tubes or columns or sheets.

U.S. Pat. application 2006/0,201,881 describes SPE devices including a plurality of packed nominally aligned capillary-channeled polymeric fibers for use as stationary phase materials. A plurality of fibers are packed together in a casing so as to provide good flow characteristics through the fibers and high surface area contact between a sample and the fibers. Different polymer compositions of the fibers permit the "chemical tuning" of the extraction process. The fibers can be physically or chemically derivatized to target specific analytes for separation from a test sample. Use of the fibers allows a wide range of liquid flow rates with very low back-pressures.

Hui-Ching Hsieh et al. describes a phosphopeptide-selective pipette tip in which titanium dioxide nanoparticles were embedded in monolithic structure photopolymerized from ethylene glycol dimethacrylate. The lowest detectable amount of phosphopeptide was estimated to be at the low femtomole level (Journal of Chromatography A, Volume 1165, Issues 1-2, 21 Sep. 2007, Pages 128-135).

Jue-Liang Hsu et al. described a method for the fabrication of disposable plastic microtips by photopolymerization. C18 reversed-phase (C18) and ion metal affinity chromatography (IMAC) beads were immobilized on a plastic pipette tip, made of polypropylene materials, by photo-initiated polymerization. The combination of IMAC tips and MALDI-MS allowed the identification of phosphopeptides based on the phosphatase assay as well as the post-source decay (Electrophoresis 2004, 25, 3840-3847).

There is a need for a new extraction pipette tip technology that can successfully be applied for desalting and/or isolating biomolecules.

In this invention, a pipette tip was fitted with a monolithic polymer structure based on organic monomers of highly porous structure. The structure was formed with a hollow center allowing the sample and other liquids to pass through the monolithic bed structure. The monolithic bed was doped with different nano-powders such as diamond, fullerenes and metal oxides ($TiO_2$ and $ZrO_2$) to add functionality to the monolith. The particles have the additional advantage of modifying the stable, pre-monolith suspension to form a stable structure in the pipette tip with a hollow center. The hollow monolith structure was stable so that the mixture can be polymerized to form the hollow monolith structure. The permeability of final polymerized extraction tips was enhanced by the hollow channel in the center of the monolithic bed.

DESCRIPTION OF THE SPECIFIC EMBODIMENTS OF THE INVENTION

Figure 1:
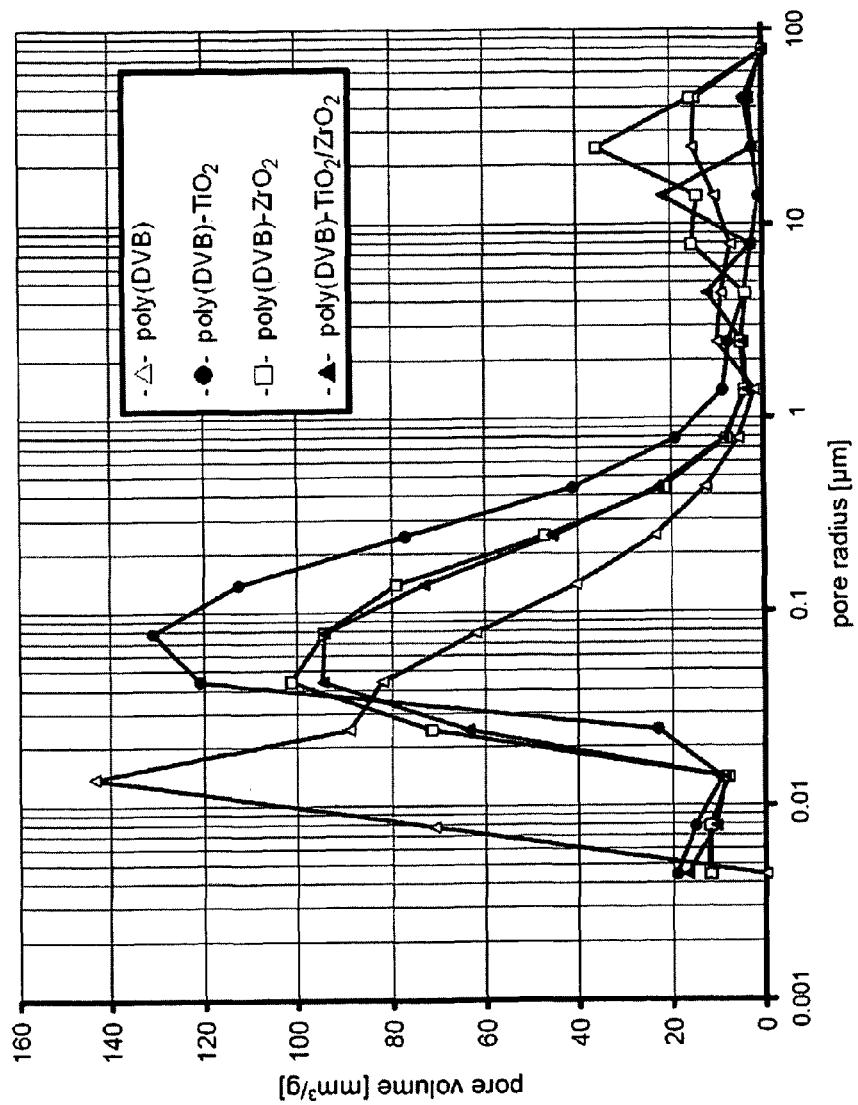
FIG. 1 shows the pore size distribution of a poly(DVB) monolith [△], poly(DVB) monolith with embedded $TiO_2$ [●], poly(DVB) with incorporated $ZrO_2$ [■] and poly(DVB) with a 1:1 mixture of $TiO_2/ZrO_2$ nanopowder [▲].

The invention relates to solid phase extraction methods and devices for extracting an analyte or group of analytes from a sample. Solid phase extraction can be described as a three step process. A solid medium is used to selectively capture an analyte from a sample solution in a single-equilibrium process. A second solution is used to wash away non-specifically bound materials. Finally, a third solution is used to release the purified analyte from the solid medium.

The analytes can include biomolecules, particularly biological macromolecules such as proteins, nucleic acids, peptides, polynucleotides, carbohydrates, lipids, metabolites, polysaccharides, phosphopeptides, protein complexes, small organic molecules and others. The process generally results in the enrichment, concentration, and/or purification of an analyte or analytes of interest. In some cases, analysis with analytical technologies such as MALDI mass spectrometry follows the extraction.

Before describing the present invention in detail, it is to be understood that this invention is not limited to specific embodiments described herein. It is also to be understood that the terminology used herein for the purpose of describing particular embodiments is not intended to be limiting. As used in this specification and the appended claims, the singular forms "a", "an" and "the" include plural referents unless the context clearly dictates otherwise. Thus, for example, reference to polymer bearing a protected carbonyl would include a polymer bearing two or more protected carbonyls, and the like. Although any methods and materials similar or equivalent to those described herein can be used in the practice or testing of the present invention, specific examples of appropriate materials and methods are described herein.

DEFINITIONS

Unless defined otherwise, all technical and scientific terms used herein have the same meaning as commonly understood by one of ordinary skill in the art to which the invention pertains. The following references provide one of skill with a general definition of many of the terms used in this invention: Singleton et al., Dictionary of Microbiology and Molecular Biology ($2^{nd}$ ed. 1994); The Cambridge Dictionary of Science and Technology (Walker ed., 1988); The Glossary of Genetics, $5^{th}$ Ed., R. Rieger et al. (eds.), Springer Verlag (1991); and Hale & Marham, The Harper Collins Dictionary of Biology (1991). As used herein, the following terms have the meanings ascribed to them unless specified otherwise.

In describing and claiming the present invention, the following terminology will be used in accordance with the definitions set out below.

DEFINITION OF TERMS

Pore: One of many small openings in a solid substance of any kind that contribute to the substance's porosity.

Polymer: Any of various chemical compounds made of smaller, identical molecules (called monomers) linked together.

Monomers: A molecule that can combine with others of the same kind to form a polymer. The monomers may contain functional groups.

Stable, pre-monolith suspension: A liquid mixture consisting of monomers, porogens, particles and optionally initiators and solvents.

Porogen: Diluents which are soluble in the stable, pre-monolith suspension, but possess poor ability to dissolve the evolving copolymer particles. The inert diluents thus act as pore-forming agents during the polymerization procedure, leaving a porous structure with sufficiently high mechanical stability after removal from the polymer network.

Initiator: a chemical compound that initiates a chemical chain reaction. Usually, it forms a free radical—an atom or molecule with at least one unpaired electron, or a group of atoms, charged or uncharged, that act as a single entity in reaction.

Nanoparticles: A nanoparticle (or nanopowder or nanocluster or nanocrystal) is a microscopic particle with at least one dimension less than 100 nm.

Particle: Any solid particle, including nanoparticles, that can be mixed into the suspension to produce the hollow monolith polymer structure. The particle generally contain functional groups.

Monolith: Single piece of porous polymer located inside the confines of a column (e.g. a pipette tip). A Hollow monolith is defined as a monolith having a hollow center portion.

Pipette tip: a pipette tip is defined herein as a tubular body having an open upper end, an open lower end and a through passageway, wherein the open upper end is adapted to engage a pump such as a pipette or liquid handling station. In some embodiments, commercially available pipette tips are used. In other embodiments, pipette tips can have any shape, including cylindrical and frustoconical. The shape of a horizontal cross-section of the pipette tip can have any geometry including circular, oval and polygonal.

Suspension: A mixture in which small particles of a substance are dispersed throughout a liquid.

Affinity group: An active chemical group having affinity for an analyte, e.g. ion exchangers, chelators, reverse phase, normal phase, enzyme, antibody, antigen.

"Analyte" refers to a component of a sample which is desirably retained and detected. The term can refer to a single component or a set of components in the sample.

"Complex" refers to analytes formed by the union of two or more analytes.

"Adsorb" refers to the detectable binding between binding functionalities of an adsorbent and an analyte.

The term "sample volume", as used herein is defined as the volume of the liquid of the original sample solution from which the analytes are separated or purified.

The terms "automated" or "automation" refer to methods or systems of operating or controlling a process by highly automatic means, as by electronic devices, reducing human intervention to a minimum.

A "liquid handler" or a "liquid handling" system, robot or device is defined herein as a machine which automatically dispenses a selected quantity of a liquid reagent using a pipette tip.

A pipette tip is only disposable column used by a pipette, liquid handler, liquid handler system, robot or devise.

The terms "dispense" and "expel" are used synonymously herein.

The term "parallel" or "parallel processing" refers to the simultaneous performance of multiple operations.

"Capture" is defined as bound or associated. A captured analyte in an analyte bound or associated with a solid support.

"Biological sample" refers to a sample derived from a virus, cell, tissue, organ or organism including, without limitation, cell, tissue or organ lysates or homogenates, or body fluid samples, such as blood, urine or cerebrospinal fluid.

The term "biomolecule" as used herein refers to molecules derived from or used with a biological system. The term includes biological macromolecules, such as proteins, peptides, carbohydrates, metabolites, polysaccharides, nucleic acids and small organic molecules.

"Biopolymer" refers to a polymer or an oligomer of biological origin, e.g., polypeptides or oligopeptides, polynucleotides or oligonucleotides, polysaccharides or oligosaccharides, polyglycerides or oligoglycerides.

"Small organic molecule" refers to organic molecules of a size comparable to those organic molecules generally used in pharmaceuticals or biological systems.

"Resolve," "resolution," or "resolution of analyte" refers to the detection of at least one analyte in a sample. Resolution includes the detection of a plurality of analytes in a sample by separation and/or subsequent differential detection. Resolution does not require the complete separation of an analyte from all other analytes in a mixture. Rather, any separation that allows the distinction between at least two analytes suffices.

"Detect" refers to identifying the presence, absence or amount of the object to be detected. "Organic biomolecule" refers to an organic molecule of biological origin, e.g., steroids, amino acids, nucleotides, sugars, polypeptides, polynucleotides, complex carbohydrates or lipids.

The present invention relates to methods for producing a hollow monolith structure within a pipette tip. The pipette tip is fitted with a monolithic structure of highly porous structure which allows sample to pass through the monolithic bed. The monolithic bed is doped with different types of particles and nano-particles e.g. diamond, fullerenes, metal-oxides. In some embodiments, isolation and identification of phosphorylated peptides from tryptic digests can be successfully performed by employing mixed $TiO_2/ZrO_2$ embedded monolithic poly(divinylbenzene) tips.

The highly porous structure of poly(divinylbenzene) which is achieved by the addition of porogens allows sample to easily pass into and through the monolithic bed and enhances the interaction of analyte and metal-oxide resulting in high capacity and selectivity. Porosity is one of the most important properties of a monolithic column, since it severely influences the chromatographic performance, the efficiency of separation as well as the specific surface area and consequently loading capacity. Porosity refers to the degree and distribution of the pore space present in a material. Open pores indicate cavities or channels. The choice of initiator and porogen is closely associated with the porosity of the resulting monolithic support.

Monolithic diamond- and fullerene-embedded tip columns showed high potential for desalting biological fluids such as human serum. Oxidized diamond nanoparticles (~size 100 nm) exhibit high affinities for peptides and proteins through hydrophilic and hydrophobic interactions. Selective adsorption of biomolecules on the diamond particles might occur due to van der Waals and/or electrostatic forces, whereas the monolithic bed provides the required porous structure including diffusion channels for efficiently entrapping analytes. The characteristics of diamond, $TiO_2$ and $ZrO_2$ are altered when particle dimensions (size and shape) are brought to the nano-level. This offers unique applications in comparison to the same bulk material. Dimensions are brought almost to the atomic levels in certain applications by arranging the material interaction atom-by-atom or molecule-by-molecule to attain unique properties. Overall surface to volume ratios are also enhanced enormously which can play an important role in bioanalytical applications. Therefore, many more biomolecules can be retained by using nano-structured materials in comparison to micro-scale materials. This was demonstrated for α-casein digest where a larger number of phosphopeptide molecules were captured with hollow monolith tip technology vs. packed bed columns.

The enrichment of biomolecules can be enhanced by increasing the pipetting cycles during the sample preparation and a higher recovery could be achieved with adequate buffer systems. To strengthen robustness and to increase reproducibility, all steps starting from tip-fabrication, analyte enrichment and purification were fully automated by liquid handling robotic systems.

The instant invention is a method of making a monolith located inside the confines of a pipette tip column. The column body is a pipette tubing having two open ends connected by an open channel, sometimes referred to as a through passageway. The pipette tubing can be in any shape, including but not limited to cylindrical or frustoconical, and of any dimensions consistent with the function of the column as described herein. A pipette tip is defined herein as any column adapted to engage a pipette or liquid handling system, either directly or indirectly. Pipette tip columns used with the MEA Personal Purification System™ (PhyNexus, Inc., San Jose) are well suited for use with the instant invention; however other suitable columns and liquid handling systems can be used.

In embodiments where the column body is a pipette tip, the end of the tip wherein the monolith is placed can take any of a number of geometries, e.g., it can be tapered or cylindrical. In some cases a cylindrical channel of relatively constant radius can be used instead of a tapered tip.

The open upper end of the column is adapted for attachment to a pump. In some embodiments of the invention the upper open end is operatively attached to a pump, whereby the pump can be used for aspirating (i.e., drawing) a fluid into the column through the open lower end of the column, and optionally for discharging (i.e., expelling) fluid out through the open lower end of the column. Thus, it is a feature certain embodiments of the present invention that fluid enters and exits the column through the same open end of the column, typically the open lower end. The fluid can be a liquid, such as a sample solution, wash solution or a desorption (elution) solution.

Various plastics make ideal column body materials. Some examples of column body materials include polysulfone, polypropylene, polyethylene, polyethyleneterephthalate, polyethersulfone, polytetrafluoroethylene, cellulose acetate, cellulose acetate butyrate, acrylonitrile PVC copolymer, polystyrene, polystyrene/acrylonitrile copolymer, polyvinylidene fluoride, glass, metal, silica, and combinations of the above listed materials.

The volume of the column body is typically in the range of at least 1 ul to at most 5 ml. Typical volumes are 2 µl, 5 µl, 10 µl, 20 µl, 100 µl, 200 µl, 250 µl, 1000 µl and 5000 µl.

The monolith used in the column preferably has an affinity or attraction for an analyte or group of analytes of interest. The term analyte as used herein can refer to any compound of interest, e.g., to be analyzed, or to a heterogeneous collection of biomolecules. Typical biomolecules include proteins, peptides, nucleic acids, lipids, carbohydrates, small organic molecules and metabolites; however, the analyte can be any biomolecule. Sources of biomolecules can be eukaryotic or prokaryotic and can include biological samples such as serum, urine, stool, cell, body fluid or excretion samples, tissue, organ, organ lysate or homogenate, blood, saliva, spinal fluid, cerebrospinal fluid, tissue culture, cell culture, bacteria, yeast, virus, etc. Alternatively, analytes can be synthesized.

The volume of the monolith used in the columns of the invention is typically 0.1 µl-80 µl or less although it can be more. The monolith can be synthesized in any size pipette tip column including 2 µl, 5 µl, 10 µl, 20 µl, 200 µl, 1 ml, 5 ml and 20 ml.

The monolith is comprised of a stable, pre-monolith suspension, which is mixture of several components: a monomer, a porogen, a particle, and optionally, an initiator. Examples of these components are listed in Table 1. Each component can also be a mixture. For example, a mixture or monomers or a mixture of particles can be used. If the monomer does not have a crosslinking moiety, it may be necessary to additionally add a crosslinker or spacer. A non-limiting list of suitable crosslinkers is iminodiacetic acid, nitrilotriacetic acid, N-carboxy-β-alanin, aspartic acid, 2-amino-2-methyl-propandiacid, 2-furan acetic acid, 5-ethyl-3-hydroxy-4-methyl-2 (5H)-furanon, tetrahydro-4-methylen-3-furan acetic acid, asparagin-acid, 2-butendi-acid, methylen-propandi-acid, 10-undecen-1-amine, 1-amino-5-hexen, N-2-propenyl-2,2, 2-trifluor acetamid, 2-butendi-acid, ethylendicarbonic acid, epoxy group like glycidyl methacrylate, 3,4-epoxybutyl acrylat, 2-methyl-2-propenyl-oxirancarbonic-acid-ester, 3-(2-methyloxiranyl)-2-propen-acid-methyl-ester, Dihydro-4-(2-propenyloxy)-2(3H)-furanon, 2-methyl-2-propensäure-oxiranylmethyl-ester, tetrahydro-3-furanyl-2-propen-acid-ester, oxiranylmethyl-2-buten-acid-ester, 1-methylethenyl-oxiran-aceticacid-ester, oxiranylmethyl-3-buten-acid-ester, (3-methyloxiranyl)-methyl-2-propen-acid-ester, 3-oxiranyl-2-propen-acid-ethyl-ester, 2-methyl-2-propenyl-oxirancarbonic-acid-ester, 2-oxiranylethyl-2-propen-acid-ester, 3-(3-butenyl)-oxirancarbonic acid, 2,3-epoxy-butteracid-allyl-ester, 2,3-epoxypropyl-croton-acid-ester, tetrahydro-2-furanyl-2-propen-acid-ester, (2-methyloxiranyl)-methyl-2-propen-acid-ester, 2-methyl-2-propen-acid-3-oxetanyl-ester, propenylchlorid, butenylchlorid, 1-brom-propen, 1-chlor-propen, 2-brom-propen, 2-chlor-propen, 4-chlor-1-buten, 4-chlor-2-buten, 3-chlor-1-buten, 2-methyl-1-chlor-1-propen, 1-chlor-2-buten, 1-chlor-1-buten, 2-chlor-3-methyl-2-buten, 3-chlor-2-methyl-2-buten, 4-chlor-2-penten, 2-chlor-2-penten, 1-chlor-1-penten, 1-chlor-3-methyl-1-buten, 1-chlor-2-methyl-1-buten, 3-chlor-2-penten, 5-chlor-2-penten 1,5-dichlor-2-penten, 4,4-dichlor-2-methyl-1-buten, 2-chlor-5-methyl-3-hexen, 3-chlor-4-methyl-1-hexen, 2-chlor-2-methyl-3-hexen and compositions of them.

To prepare a hollow monolith within a pipette tip column, the pipette tip is attached to a pump such as a pipette or liquid handling robot and the stable, pre-monolith suspension is aspirated into the pipette tip through the open lower end. Alternatively, the stable, pre-monolith suspension can be introduced into the open upper end of the pipette tip. The suspension may be polymerized at this step in the pipette tip without forming the hollow monolith structure. Next, a hollow structure is formed inside the pipette tip by either allowing the center portion of the suspension to drain out of the column or by pushing the center portion of the mix of the column. Under normal pipetting conditions, the entire suspension would drain from the column. Also, under normal circumstances monomers, solvents, porogens and mixtures all drain from the pipette tip as would be expected since pipetting is often used to transfer mixtures of these types. However, the addition of the particles to the suspension will under some circumstances, change the properties of the suspension so that a stable structure of monolith with a hollow center can be formed inside the tip before polymerization. The particles in the suspension maintain a sort of solid support for the hollow monolith structure until the polymerization can occur. This pre-hollow monolith structure is formed against or coated to the walls. In some embodiments, the inner surface of the pipette tip is considered coated with the pre-monolith suspension.

The center portion of suspension can be removed by any one of a number of draining methods including draining, centrifugation, rotation, gravity, sedimentation, application of vacuum or aspiration and expulsion of the polymer stable, pre-monolith suspension. At this stage, a pre-hollow monolith is formed. A hollow center is maintained in the suspension until the polymerization can be completed and a hollow monolith structure is formed. In some embodiments, heat is used to promote polymerization. In other embodiments, light or radiation, such as gamma radiation are used to promote polymerization.

The conditions needed to maintain the hollow structure within the pipette tip are now completely understood or completely predictable. A stable, pre-monolith suspension containing particles that can form the hollow monolith inside the pipette tip is produced on a trial and error basis. It is known that ability to form the hollow structure is dependent on particle size and concentration. Smaller particles make more stable suspensions. The particles can be nano-particles or they can be micro-scale particles. The pre-monolith suspension must be formed correctly to achieve stability. Uneven distribution of particles results in a suspension that is too thin. If the suspension is too thick, the suspension will drain excessively during the polymerization and the tip will clog. The size of the open lower end of the pipette tip must be considered for each suspension. If the opening is too large, too much of suspension will drain.

The particles sizes are in the range of 1 nm to 20 um. In some embodiments, the particle size is in the range of 1 nanometer to 100 micrometers, 20 nanometers to 5 micrometers or 100 nanometers to 2 micrometers.

The concentration range of particles used in the stable, pre-monolith suspension ranges from 0.02 to 3.0 mg solids per µl volume of monomers and porogens with 0.2-0.4 used many embodiments. The mass amount of solids needed depends on the particle size and shape and density of the materials. To a lesser extent the mass amount needed depends on the liquid density and viscosity.

Affinity extractions or preparations use a technique in which a bio-specific ligand is prepared by coupling a ligand specific for the analyte (such as an enzyme, antigen, or hormone) to the monolith. This immobilized ligand will interact selectively with molecules that can bind to it. Molecules that will not bind elute unretained. The interaction is selective and reversible. In some embodiments, the particles within the monolith are additionally comprised of a bio-specific ligand. In other embodiments, the bio-specific ligand is attached to the monomer. In other embodiments, the bio-specific ligand is attached to both the monomer and particle.

Bio-specific ligands can be based on the following types of interactions or groups: polar, non-polar, ionic, affinity, bio-affinity, biochemical, specific and metal chelating groups and/or combinations of them. Examples of suitable groups include carbon-binding groups, epoxy, halogens, amino groups, hydroxy groups, acid groups, acid chlorides, cyanide groups, aldehyde groups, sulfate groups, sulfonate groups, phosphate groups, metal chelate groups (e.g. metal-NTA chelate such as Nickel NTA, Copper NTA, Iron NTA, Cobalt NTA, Zinc NTA, metal-IDA chelate such as Nickel IDA, Copper IDA, Iron IDA, Cobalt IDA and metal-CMA (carboxymethylated aspartate) chelate such as Nickel CMA, Copper CMA, Iron CMA, Cobalt CMA, and Zinc CMA), other chelating metals such as aluminum, manganese, cobalt, zinc, gallium, nickel, Fc regions and/or Fab regions such as Protein G, Protein A, Protein A/G, and Protein L, thioether, biotin, thiols, nucleic acids, (e.g. nucleotides, oligonucleotides, polynucleotides and their analogs (e.g., ATP)), sugars, proteins, chelating metals, glutathione surfaces, lectin surface-heparin surface-avidin or streptavidin surface, a peptide or peptide analog (e.g., that binds to a protease or other enzyme that acts upon polypeptides) and compositions of them.

In some embodiments of the invention, the affinity binding reagent is one that recognizes one or more of the many affinity groups used as affinity tags in recombinant fusion proteins. In other embodiments of the invention solid support materials are employed that are generally less specific than the affinity binding agents discussed above. These chemistries are still often quite useful. Table I shows different combinations used of particles and monomers with various initiators and porogens. Virtually any combination of particles, monomers, initiators and porogens can be used provided a stable, pre-monolith suspension can be formed from the mixture. Other solid particles that can be used include calcium phosphate, calcium carbonate, iron oxide, copper sulfate, alumina, etc. Virtually any metal salt can be used. Other solid particles include organic materials cellulose, polymeric particles, organic solids, etc. Particles may be from the group consisting of: silica, metal oxides, metals, ceramics, synthetic polymers, biopolymers, and allotropes of carbon. They may be allotropes of carbon are fullerenes, diamond, graphite, nanotubes, or nanowires. They may be mixtures from the group consisting of: silica, metal oxides, metals, ceramics, synthetic polymers, biopolymers, and allotropes of carbon or they may be any mixture of two or more types of solid particles.

TABLE I

| Particles | monomers | Initiators | porogens |
|---|---|---|---|
| Metal oxides | Isobutylene | Thermal initiators | Decanol |
| Zirconium oxide | Diisobutylene | 4,4'-Azobis(4-cyanovaleric acid) ≧75% | Toluene |
| Manganese oxide | Acrylic Monomers | 1,1'-Azobis(cyclohexanecarbonitrile) 98% | Hexanol |
| Tin oxide | Acrylic Acid | 2,2'-Azobis(2-methylpropionitrile) 98% | n-butanol |
| Titanium oxide | Acrylamide | Benzoyl peroxide | sec-butanol |
| Indium oxide | Acrylonitrile | 2,2-Bis(tert-butylperoxy)butane | 2-ethyl-hexanol |
| Gallium oxide | Methyl Acrylate | 2,5-Bis(tert-butylperoxy)-2,5-dimethylhexane | 4-methyl-2-pentanol |
| | Ethyl Acrylate | Bis[1-(tert-butylperoxy)-1-methylethyl]benzene | 2-ethylhexylacetate |
| | Butyl Acrylate | tert-Butyl hydroperoxide Solution 5.0-6.0 M in decane | methyl oleate |
| Desalting devices | Benzyl acrylate | tert-Butyl peracetate Solution | dibutyl sebacate |
| Diamond | Glycidyl acrylate | tert-Butyl peroxide 98% | dibutyl adipate |
| Fullerene silica | 4-tert-Butylphenol | tert-Butyl peroxybenzoate | dibutyl carbonate |

TABLE I-continued

| Particles | monomers | Initiators | porogens |
| --- | --- | --- | --- |
| Fullerene | 1.3 Dioxolane | Cumene hydroperoxide | alkyl ketones |
| Palladium nanoparticles entrapped in aluminum hydroxide matrix | Isophthalic acid | Dicumyl peroxide | diisobutyl ketone |
| Rhodium nanoparticles entrapped in aluminum hydroxide matrix | Methacrylic acid | Lauroyl peroxide | methyl isobutyl ketone |
| functionalized gold nanoparticles | 2-(dimethylamino)ethyl ester | Peracetic acid Solution 32 wt. % in dilute acetic acid | alkyl carboxylic acids |
| functionalized silver nanoparticles | 3-Methyl-1-butene | Potassium persulfate ACS reagent, ≧99.0% | |
| Magnetic ironoxide nanoparticles | Perfluoropropyl perfluorovinyl ether | Photoinitiators | |
| Silica | Triallylamine | Acetophenone | |
| | Acrylic acid, 2-ethylhexyl ester | Diphenyl(2,4,6-trimethylbenzoyl)phosphine oxide | |
| | 1,2,4-Benzenetricarboxylic acid | 4,4'-Dimethoxybenzoin | |
| | Benzoguanamine | Anthraquinone | |
| | 1,4-Butanediol | Anthraquinone-2-sulfonic acid Sodium salt | |
| | Caprolactone | Benzene-chromium(0) tricarbonyl | |
| | Crotonic acid | 4-(Boc-aminomethyl)phenyl isothiocyanate | |
| | 2,4-Diamino-6-phenyl-1,3,5-triazine | Benzil | |
| | Dicyclopentadiene | Benzoin | |
| | 3,3'-Dimethyl-4-4'-diaminodicyclo-hexylmethane | Benzoin ethyl ether | |
| | Divinylbenzene | Benzoin isobutyl ether technical grade | |
| | Dodecanedioic acid | Benzoin methyl ether | |
| | 5-Ethylidenebicyclo[2.2.1]hept-2-ene | Benzophenone | |
| | 1,4-Hexadiene | Benzophenone/1-hydroxycyclohexyl phenyl ketone | |
| | 1,6-Hexanediol | Benzophenone-3,3',4,4'-tetracarboxylic dianhydride | |
| | Methacrylic acid, 2-sulphoethyl ester | 4-Benzoylbiphenyl | |
| | Methacrylic acid, sulphopropyl ester | -Benzyl-2-(dimethylamino)-4'-morpholinobutyrophenone | |
| | N-methylolmethacrylamide | 4,4'-Bis(diethylamino)benzophenone | |
| | Alpha-methylstyrene | Michler's ketone | |
| | Trimellitic acid | (±)-Camphorquinone | |
| | Trimellitic anhydride | 2-Chlorothioxanthen-9-one | |
| | 1,1,1-Trimethylopropane trimethacrylate | 5-Dibenzosuberenone | |
| | Vinylpyrrolidone | 2,2-Diethoxyacetophenone | |
| | Glycidyl Methacrylate | 4,4'-Dihydroxybenzophenone | |
| | 2,4,6-Trimethylstyrene | 2,2-Dimethoxy-2-phenylacetophenone | |
| | 2,4-Dimethylstyrene | 4-(Dimethylamino)benzophenone | |
| | 2,5-Dimethylstyrene | 4,4'-Dimethylbenzil | |
| | 2,6-Dichlorostyrene | 3,4-Dimethylbenzophenone | |

TABLE I-continued

| Particles | monomers | Initiators | porogens |
|---|---|---|---|
| | Glycidyl 2-methylphenyl | Diphenyl(2,4,6-trimethylbenzoyl)phosphine oxide/2-hydroxy-2-methylpropiophenone | |
| | Glycidyl 4-methoxyphenyl ether | 4'-Ethoxyacetophenone | |
| | Glycidyl hexadecyl ether | 2-Ethylanthraquinone | |
| | Glycidyl isobutyl ether | Ferrocene | |
| | Glycidyl isopropyl ether | 3'-Hydroxyacetophenone | |
| | Glycidyl methacrylate | 4'-Hydroxyacetophenone | |
| | 2,5-Dibromo-3-octylthiophene | 3-Hydroxybenzophenone | |
| | 2,5-Dibromo-3-butylthiophene | 4-Hydroxybenzophenone | |
| | 2,5-Dibromo-3-phenylthiophene | 1-Hydroxycyclohexyl phenyl ketone | |
| | 1,4-Naphthalenedicarboxylic acid | 2-Hydroxy-2-methylpropiophenone | |
| | 2,2'-Iminodibenzoic acid | 2-Methylbenzophenone | |
| | 2-Bromoterephthalic acid | 3-Methylbenzophenone | |
| | 2-Methoxyisophthalic acid | Methyl benzoylformate | |
| | Allyl acetate | 2-Methyl-4'-(methylthio)-2-morpholinopropiophenone | |
| | 1,12-Diisocyanatododecane | 9,10-Phenanthrenequinone | |
| | 1,12-Diisocyanatododecane | 4'-Phenoxyacetophenone | |
| | 4-Diaminopyrimidine | Thioxanthen-9-one | |
| | Ethylenediaminetetra acetic dianhydride | Triarylsulfonium hexafluorophosphate salts, | |
| | 1,3,5-Trimethylhexahydro-1,3,5-triazine | 3-Mercapto-1-propanol | |
| | 1,4,8,11-Tetramethyl-1,4,8,11-tetraazacyclotetradecane | 11-Mercapto-1-undecanol | |
| | | 1-Mercapto-2-propanol | |
| | | 3-Mercapto-2-butanol | |

Apparatus and Methods for Using the Columns

Although the methods described below frequently refer to a single pipette tip column, or column, it is to be understood that the methods are often performed in parallel. That is, multiple samples are prepared simultaneously.

Generally the first step in a preparation procedure of the invention will involve introducing a sample solution containing an analyte of interest into a pipette tip column comprised of a hollow monolith. The sample can be conveniently introduced into the solid support by aspirating and dispensing the solution through the column using a liquid handling system. Note that the volume of sample solution can be much larger than the monolith bed volume. The sample solution can optionally be aspirated and dispensed repeatedly (pumped back and forth through the monolith more than one time). This can improve adsorption of analyte, which can be particularly useful in cases where the analyte is of low abundance.

After the sample solution has been introduced into the monolith bed and analyte allowed to adsorb, the sample solution is substantially evacuated from the bed, leaving the bound analyte. It is not necessary that all sample solution be evacuated from the monolith bed, but diligence in removing the solution can improve the purity of the final product. An optional wash step between the adsorption and desorption steps can also improve the purity of the final product. Typically water or a buffer is used for the wash solution. The wash solution can optionally be aspirated and dispensed repeatedly (pumped back and forth through the monolith more than one time). The wash solution is preferably one that will, with a minimal desorption of the analyte of interest, remove excess sample materials, lightly adsorbed or non-specifically adsorbed materials. The wash cycle can include solvent or solvents having a specific pH, or containing components that promote removal of materials that interact lightly with the solid support. In some cases, several wash solvents might be used in succession to remove specific material, e.g., PBS followed by water. These cycles can be repeated as many times as necessary. In other cases, a wash cycle can be omitted.

The desorption solvent will vary depending upon the nature of the analyte and the functional group present on the monolith. In some cases desorption is achieved by a change in pH or ionic strength, e.g., by using low pH or high ionic strength desorption solution. A suitable desorption solution can be arrived at using available knowledge by one of skill in the art. Sometimes in order to improve recovery it is desirable to pass the desorption solvent through the monolith multiple times, e.g., by repeatedly aspirating and discharging the desorption solvent through the lower end of the column. Step elutions can be performed to remove materials of interest in a sequential manner. The volume of desorption solvent used can be very small. The use of small volumes of desorption solution enables one to achieve high concentrations of eluted analyte.

Alternatively, the volume of desorption solvent used can be quantified in terms of percent of the monolith volume (i.e., the total volume of monolith plus the pores). For example, ranges of desorption solvent volumes appropriate for use with the invention can have a lower limit of 1%, 5%, 10%, 15%, 20%, 30%, 40%, 50%, 60%, 70%, 80%, 90%, 100%, 150%, 200% or 300% of the monolith volume, and an upper limit of 50%, 100%, 200%, 300%, 400%, 500%, 500%, 600%, 700%, 800%, or 1000% of the monolith volume, e.g., 10 to 200% of the monolith volume, 20 to 100% of the monolith volume 10 to 50%, 100% to 500%, 200 to 1000%, etc., of the monolith volume.

In some embodiments of the invention, the amount of desorption solvent introduced into the column is less than 100 µL, less than 20 µL, less than 15 µL, less than 10 µL, less than 5 µL, or less than 1 uL. For example, ranges of desorption solvent volumes appropriate for use with the invention can have a lower limit of 0.1 µL, 0.2 µL, 0.3 µL, 0.5 µL, 1 µL, 2 µL, 3 µL, 5 µL, or 10 µL, and an upper limit of 2 µL, 3 µL, 5 µL, 10 µL, 15 µL, 20 µL, 30 µL, 50 µL, or 100 µL, e.g., in between 1 and 15 µL, 0.1 and 10 µL, or 0.1 and 2 µL.

Columns of the invention can accommodate a variety of flow rates, and the invention provides methods employing a wide range of flow rates, oftentimes varying at different steps of the method. In some cases, it is desirable to perform one or more steps of a purification process at a relatively slow flow rate, e.g., the loading and/or wash steps, to maximize binding of an analyte of interest to a solid support. To facilitate such methods, in certain embodiments the invention provides a pipette comprising a column body; a microprocessor; an electrically driven actuator disposed within the body, the actuator in communication with and controlled by the microprocessor; a displacement assembly including a displacing piston moveable within one end of a displacement cylinder having a displacement chamber and having another end with an aperture, wherein said displacing piston is connected to and controlled by said actuator; and a pipette tip in communication with said aperture, wherein the microprocessor is programmable to cause movement of the piston in the cylinder at a rate that results in drawing a liquid into the pipette tip at a desired flow when the tip is in communication with the liquid. The flow rate can be relatively slow, such as the slow flow rates described above, e.g., between about 0.1 and 4 mL/min. In some embodiments, the process is controlled by a liquid handling system comprised of a microprocessor in communication with a multichannel pipettor.

In some embodiments, the microprocessor is external to the body of the pipettor, e.g., an external PC programmed to control a sample processing procedure. In some embodiments the piston is driven by a motor, e.g., a stepper motor.

The invention provides a pipettor (such as a multi-channel pipettor or liquid handling robot) suitable for acting as the pump in methods such as those described above. In some embodiments the pipettor comprises an electrically driven actuator. The electrically driven actuator can be controlled by a microprocessor, e.g., a programmable microprocessor. In various embodiments the microprocessor can be either internal or external to the pipettor body. In certain embodiments the microprocessor is programmed to pass a pre-selected volume of solution through the solid support at a pre-selected flow rate.

Multiplexing

In some embodiments of the invention a plurality of columns is run in a parallel fashion, e.g., multiplexed. This allows for the simultaneous, parallel processing and spotting of multiple samples. In some embodiments, the method is applied concurrently and in parallel to multiple pipette tip columns sealingly attached to a multi-channel pipettor (such as a robotic liquid handling system), Multiplexing can be accomplished by use of the columns, wells or tubes using a pipetting robot or liquid handling system such as the MEA Personal Purification System™ from PhyNexus, Inc., San Jose. Other liquid handling systems that can be used with the methods of the instant invention include those manufactured by Zymark (e.g., the Sci-Clone sample handler), Tecan (e.g., Freedom EVO and Genesis systems) or Cartesian Dispensing (e.g., the Honeybee benchtop system), Packard (e.g., the MiniTrak5, Evolution, Platetrack, or Apricot), Beckman (e.g., the FX-96) and Matrix (e.g., the Plate Mate 2 or SerialMate), Caliper (e.g. Sciclone), Perkin Elmer (e.g. MiniTrak), Velocity 11 (e.g. Bravo), Hamilton (e.g. Star) and others.

When using a multiplexed system, it may be desirable to program delays into the software controlling the protocol. When several columns are operated in parallel and the sample is very viscous, each column may have a slightly different back pressure. As a result, the flow rate of a liquid through each column may vary when vacuum or pressure is applied to the columns. One means of compensating for the different flow rates is the incorporation of delays to equalize the vacuum or pressure and thus equalize the total amount of liquid expelled or aspirated. Pauses can be used at any time during the protocol, e.g. while aspirating, dispensing, or between an aspiration and a dispense step.

The extraction process can be automated, for example by using software to program the computer controller to control the pumping, e.g., the volumes, flow rates, delays, and number of cycles.

In some embodiments, the invention provides a multiplexed preparation system comprising a plurality of columns of the invention, e.g., pipette tip columns comprised of a monolith positioned within the column. The system can include a pump or pumps in operative engagement with the columns, useful for pumping fluid through the columns in a multiplex fashion, i.e., concurrently. In some embodiments, each column is addressable. The term "addressable" refers to the ability of the fluid manipulation mechanism, e.g., the pumps, to individually address each column. An addressable column is one in which the flow of fluid through the column can be controlled independently from the flow through any other column which may be operated in parallel. In practice, this means that the pumping means in at least one of the steps is in contact and control of each individual column independent of all the other columns. For example, when syringe pumps are used, i.e., pumps capable of manipulating fluid within the column by the application of positive or negative pressure, then separate syringes are used at each column, as opposed to a single vacuum attached to multiple syringes. Because the columns are addressable, a controlled amount of liquid can be accurately manipulated in each column. In a non-addressable system, such as where a single pump is applied to multiple columns, the liquid handling can be less precise. For example, if the back pressure differs between multiplexed columns, then the amount of liquid entering each column and/or the flow rate can vary substantially in a non-addressable system. Various embodiments of the invention can also include samples racks, instrumentation for controlling fluid flow, e.g., for pump control, etc. The controller can be manually operated or operated by means of a computer. The computerized control is typically driven by the appropriate software, which can be programmable, e.g., by means of user-defined scripts.

The invention also provides software for implementing the methods of the invention. For example, the software can be programmed to control manipulation of solutions and addressing of columns into sample vials, collection vials, for spotting or introduction into some analytical device for further processing.

The invention also includes kits comprising one or more reagents and/or articles for use in a process relating to solid phase extraction, e.g., buffers, standards, solutions, columns, sample containers, etc.

Analysis of Phosphorylated Peptides and Proteins

In proteomics, the analysis of phosphorylated peptides and proteins is highly demanded, since protein phosphorylation is known as the most common post-translational modification found in nearly all cellular processes including signal transduction, gene expression and metabolism. Approximately one-third of all mammalian cellular proteins can be phosphorylated and abnormal phosphorylation is recognized as a cause or consequence of many human diseases. Phosphorylation of serine accounts for approximately 90% of these modifications, whereas phosphorylation of threonine and tyrosine residues accounting for 10% and 0.1% of the total, respectively. Understanding of cellular regulation will be only achieved by getting more knowledge about the sites of protein phosphorylation and the correlation of phosphate residency with metabolic changes.

A huge difficulty in determining the state of protein phosphorylation is the enormous complexity of the proteome and the occurrence of potentially important phosphoproteins at very low concentrations. Hence, a number of different strategies have been already introduced to separate phosphorylated from non-phosphorylated peptides and proteins. Especially chromatographic approaches based on solid phase extraction (SPE) are considered to be most popular in this regard. Commonly applied approaches involve immobilized metal ion affinity chromatography (IMAC), which was first introduced by Porath et al. in 1975. For creating an IMAC support, metal ions, such as $Fe^{3+}$, $Zn^{2+}$, $Cu^{2+}$ or $Ni^{2+}$ are first bound to chelating ligands such as iminodiacetic acid (IDA) or nitrilotriacetic acid (NTA) according to the hard and soft acids and bases (HSAB)-principle postulated by Pearson. The chelated metal ions show variations in affinity toward proteins, which can be predicted using the HSAB principle. The binding interaction with peptides and proteins is strongly pH dependent. The bound biomolecules can be then eluted from the IMAC support by varying the pH and increasing the ionic strength of the buffer or by employing chelating agents such as ethylenediamine tetraacetic acid (EDTA) or imidazole. Most commonly applied methods for the enrichment of phosphorylated peptides include IMAC supports based on $Ga^{2+}$ or $Fe^{3+}$-ions which are chelated on solid matrices like agarose and cellulose or silica. Another approach is employing synthetic polymer beads based on poly(GMA/DVB) for the selective isolation of phosphopeptides. GMA/DVB copolymer was first modified with IDA and loaded with $Fe^{3+}$ ions to form an IMAC support material. Poly(GMA/DVB)-IDA-$Fe^{3+}$ revealed high recovery rates (approximately 92%) and high selectivity for binding phosphopeptides from various kinds of samples, including a tryptic digest of the in vitro phosphorylated protein GST-ERK2 down to the low picomole level.

Enrichment of phosphorylated compounds is often carried out in conjunction with further mass spectrometric analysis, in particular matrix-assisted laser desorption/ionization (MALDI) time-of-flight (TOF) MS, because it is sensitive and probably most compatible with biological buffers. Nevertheless a prior desalting step of enriched phosphopeptides is usually unavoidable, due to the signal suppressing effects of salts and buffer residues during MS analysis, especially for very low-concentrated compounds. A desalting step of eluted biomolecules will serve to eliminate interferences and to increase signals in peptide identification experiments. Although $Fe^{3+}$-IMAC is a well studied affinity device to isolate phosphopeptides, there are some drawbacks which are largely based on unspecific bindings due to ionic interactions. This can occur during the purification steps and might lead to an additional enrichment of glutamic and aspartic acid residual rich compounds. Moreover other amino acid residues like cysteine and histidine might also interact with the IMAC support by decreasing the selectivity of phosphorylated peptides and proteins. However, this problem can be overcome by converting the carboxyl groups to methyl esters, but might lead to unwanted peptide modifications. Recently, several approaches have been introduced demonstrating the unique ability of metal oxides such as titanium dioxide ($TiO_2$) or zirconium dioxide ($ZrO_2$) to selectively retain phosphopeptides from complex biological mixtures. This metal oxide based approach is commonly referred as metal oxide affinity chromatography (MOAC). The binding of phosphate anions to the surface of $TiO_2$ and $ZrO_2$ is a bridging bi-dentate surface complex and the coordination geometry differs from that of an optimal binding site for a substituted carboxylic group. Comparative studies of $Fe^{3+}$-IMAC and $TiO_2$ were carried out by Cantin et al. which showed a higher efficiency for phosphopeptide enrichment in case of $TiO_2$.

In an embodiment of the instant invention poly(divinylbenzene) based extraction tips were designed and successfully applied for the enrichment of phosphorylated peptides. The monolithic bed was either doped with $TiO_2$, $ZrO_2$ or a mixture of $TiO_2$ and $ZrO_2$ in form of nano-powders. The properties and advantages of this material are discussed in detail by its application upon tryptic protein digests.

EXAMPLES

Example 1

Preparation of Poly(DVB) Based and $TiO_2$- or Mixed $TiO_2/ZrO_2$-Embedded Extraction Tips For the preparation of $TiO_2$ and $ZrO_2$ doped poly(divinylbenzene) pipette tips, a polymerization mixture comprising divinylbenzene (DVB) (150 μL; free of inhibitors), distilled decanol (150 μL), anhydrous toluene (100 μL) and AIBN (10 mg) were prepared. In the case of poly(divinylbenzene)-$TiO_2$ tips 220 μL of the polymerization mixture were added to a glass vial containing 65 mg of $TiO_2$ nanopowder (<100 nm) to form the stable, pre-monolith suspension. Regarding poly(divinylbenzene)-$ZrO_2/TiO_2$ tips, a 200 μL aliquot of the same polymerization mixture was spiked with $ZrO_2$ and $TiO_2$ nanopowders, 30 mg each, forming the stable, pre-monolith suspension. The mixtures were vortexed for 5 min and ultrasonicated for 1 min at room temperature. Two microliters of each stable, pre-monolith suspension were aspirated into 10 μl pipette tips. The center of the suspension was expelled, making a pre-hollow monolith suspension inside the tip. The tips were then placed into an oven for 2.5 hours at 80° C. After polymerization, the extraction tips were extensively washed with ACN and MeOH to remove all unreacted components and porogens.

Example 2

Pore Size and Pore Volume of Four Different DVB Monoliths

Due to their open-channel structure, monoliths possess high permeability, allowing the application of enhanced flow rates at moderate back pressure, which is especially required when fitted into pipette-tips. In case of $TiO_2$ and $ZrO_2$-embedded poly(DVB) tips, in addition to making a hollow structure, a highly porous monolithic structure is achieved by the addition of decanol and toluene as porogens. Pore size and pore volume of four different DVB monoliths were investigated by MIP measurements: pure poly(DVB) [△], poly(DVB) doped with $TiO_2$ [●], as well as doped with $ZrO_2$ [■] and a 1:1 mixture of $TiO_2/ZrO_2$ [▲]. Depending on the size of the pores, mercury intrudes the fraction of open pores at a given applied pressure. The change in volume, which is indicated on the scale of the dilatometer, is registered at each applied pressure, resulting in a graph, presented in FIG. 1.

Since the pressure is inversely proportional to the pore radius, the size of pores can be plotted against the cumulative volume, which is described as the total volume of mercury penetrating the porous material at a given pressure. Table 2 shows the values for the average pore radius, the total porosity and the specific surface of all mentioned extraction materials. For pure poly(divinyl benzene) monolith, MIP measurements provided a total porosity of 46% and an average pore radius of 12 nm. In case of nanoparticle-embedded monoliths, the average pore radius increased to 52 nm, whereas the total porosity decreased by 5 to 7%. The specific surface area was highest for pure poly(DVB) (53.6 $m^2/g$) and decreased to almost the half by doping the monolith with nanopowders.

TABLE 2

| Monolith | Mean pore diameter (nm) | Surface area (m2/g) | Total porosity (%) |
|---|---|---|---|
| Poly(DVB) | 12 | 53.6 | 46.0 |
| Poly(DVB)-TiO2 | 52 | 27.8 | 35.6 |
| Poly(DVB)-ZrO2 | 52 | 24.7 | 41.9 |
| Poly(DVB)-ZrO2/TiO2 | 52 | 25.8 | 38.9 |

Example 3

Enrichment of Phosphopeptides by $TiO_2$- or Mixed $TiO_2/Zro_2$-Embedded Extraction Tips Monolithic tips were first activated with ACN/0.1% TFA for two times by aspirating (flow rate, 0.5 mL/min) and expelling a volume of 10 µL (flow rate, 0.03 mL/min). Afterwards tips were equilibrated in the same manner by applying 10 µL $H_2O$/0.1% TFA two times. For sample-loading 10 µL of the protein digest solutions were aspirated into the tip and dispensed by eight to ten times repetition (same flow rates). All non-phosphorylated peptides were washed away by applying two washing steps with 20 µL of 50% ACN/0.1% TFA containing DHB (20 g/L) by cycling the washing solution ten times. Additionally, two washing steps with 80% ACN/0.1% TFA and one washing step with deionized water were performed. Finally, elution was carried out by aspirating 5 µL of 20% ACN/0.5% $NH_4OH$ (pH 10.5) and dispensing the eluate into a separate centrifuge tube (0.5 mL), by repeating the process five to ten times (florate, 0.01 mL/min).

Example 4

Preparation of Poly(DVB) Based Diamond-Embedded Extraction Tips

Diamond-embedded hollow monolithic pipette tips were prepared from a polymerization mixture containing distilled GMA (150 µL), DVB (150 µL; free of inhibitors), distilled decanol (150 µL) and AIBN (20 mg). Then, 200 µL of the polymerization mixture was added to a glass vial containing 20 mg of diamond nanopowder <10 nm). Next, anhydrous toluene (50 µL) was added to form the stable pre-monolith suspension. The mixture was vortexed for 5 min and ultrasonicated for 1 min at room temperature. One microliter of the suspended polymerization mixture was aspirated in 10 µL pipette tips (Eppendorf). The center of the pre-monolith suspension drained out, forming the pre-hollow monolith structure in the tip. The tips were placed into a heating chamber at 75° C. for 2.5 hours. After the polymerization process, the hollow monolith was formed. The pipette tips were extensively washed with ACN and MeOH to remove all unreacted components.

Example 5

Desalting of Biological Samples by Diamond-Embedded Extraction Tips

Desalting of human serum was compared using a micro column based on pure poly(GMA/DVB) versus doping the monolithic bed with diamond nano-beads. Extraction tips were first activated with ACN/0.1% TFA for three times by aspirating and expelling a volume of 10 µL. In a further step tips were equilibrated in the same manner by applying three times 0.1% TFA solution. For sample-loading, 10 µL of human raw serum was diluted in 90 µL of 0.1% TFA and 10 µL of the diluted serum was aspirated into the tip and dispensed by eight to ten times repetition. In a further step all salts were washed away by applying seven washing steps with deionized water by discarding water each time. Finally, elution was performed by aspirating 5 µL of ACN/0.1% TFA solution into the extraction tip and dispensing the eluate into a separate centrifuge tube (0.5 mL), repeating the process for five times. One microliter of the eluate was then spotted onto a MALDI steel target (Bruker Daltonics GmbH, Bremen, Germany) followed by adding 1 µL of α-Cyano-4-hydroxycinnamic acid in 50% (v/v) ACN, 0.1% TFA.

Figure 5:
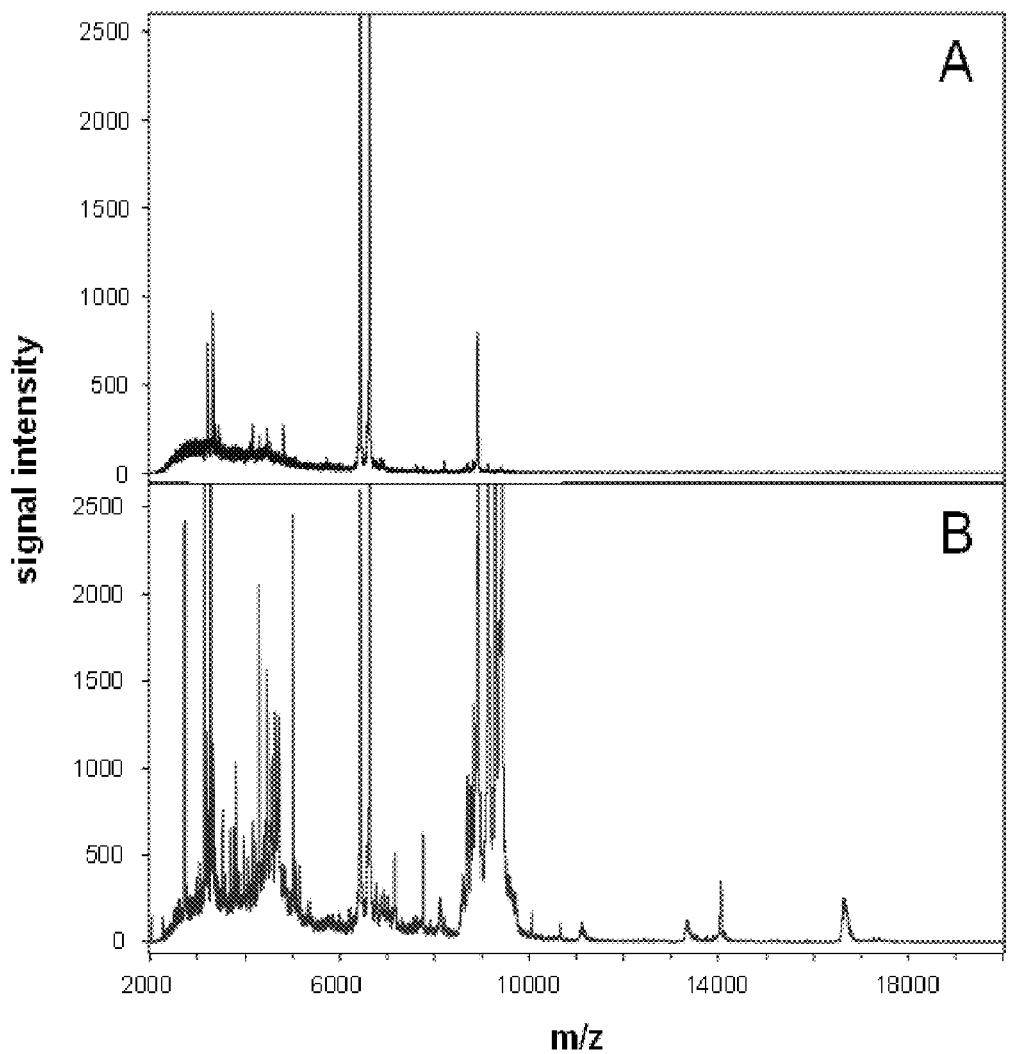
FIG. 5 is the MALDI mass spectrum obtained from analysis of a human serum sample desalted on (A) pure monolithic poly(GMA/DVB) tip and (B) the corresponding spectrum by applying a diamond-embedded poly(GMA/DVB) based micro column.

FIG. 5 shows a MALDI mass spectrometric analysis of a human serum sample desalted on (A) pure monolithic poly (GMA/DVB) tip and (B) the corresponding spectrum by applying a diamond-embedded poly(GMA/DVB) based micro column. The spectra obtained from the pure monolithic poly(GMA/DVB) shows sharp signals and good S/N ratios, however the peak capacity is less than the signal obtained when the monolith was doped with diamond nano-beads.

Example 6

Isolation of Phosphorylated Peptides from α- and β-Casein

Tryptic digests of α- and β-casein were prepared and phosphorylated peptides were enriched with either poly(DVB)-$TiO_2$ or $ZrO_2/TiO_2$-embedded monolithic extraction tips.

Figure 2:
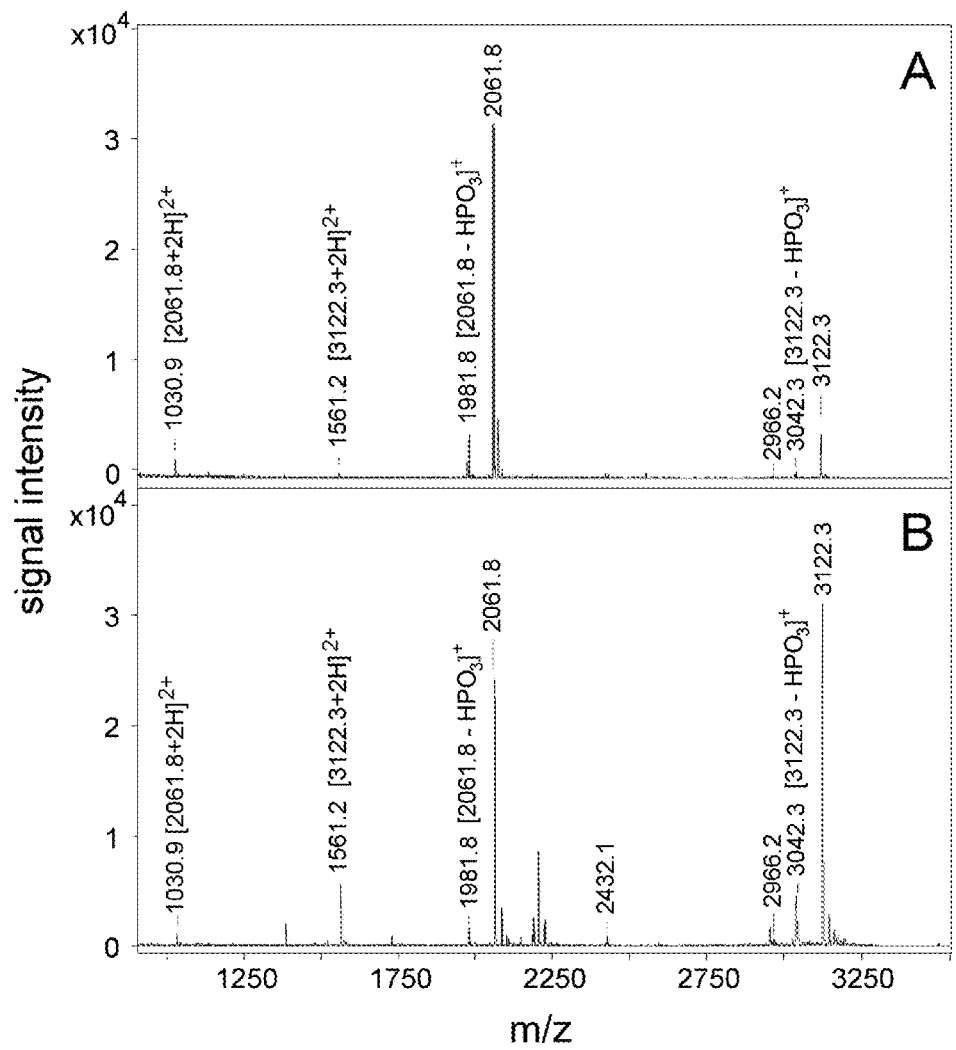
FIG. 2 is the MALDI-MS spectra, recorded after enrichment of β-casein digest with (A) poly(DVB)-$TiO_2$ extraction tips and (B) mixed poly(DVB)-$TiO_2/ZrO_2$ tips.

Four phosphorylated peptides were isolated from β-casein tryptic digest (FIG. 2A and Table 3) and sixteen were isolated from an α-casein digest (FIG. 3A) by employing poly(DVB)-$TiO_2$-embedded monolithic extraction tips. The total number of recovered phosphopeptides for β-casein and α-casein digests including their corresponding signal-to-noise (S/N) ratios are listed in Table 3.

Figure 3:
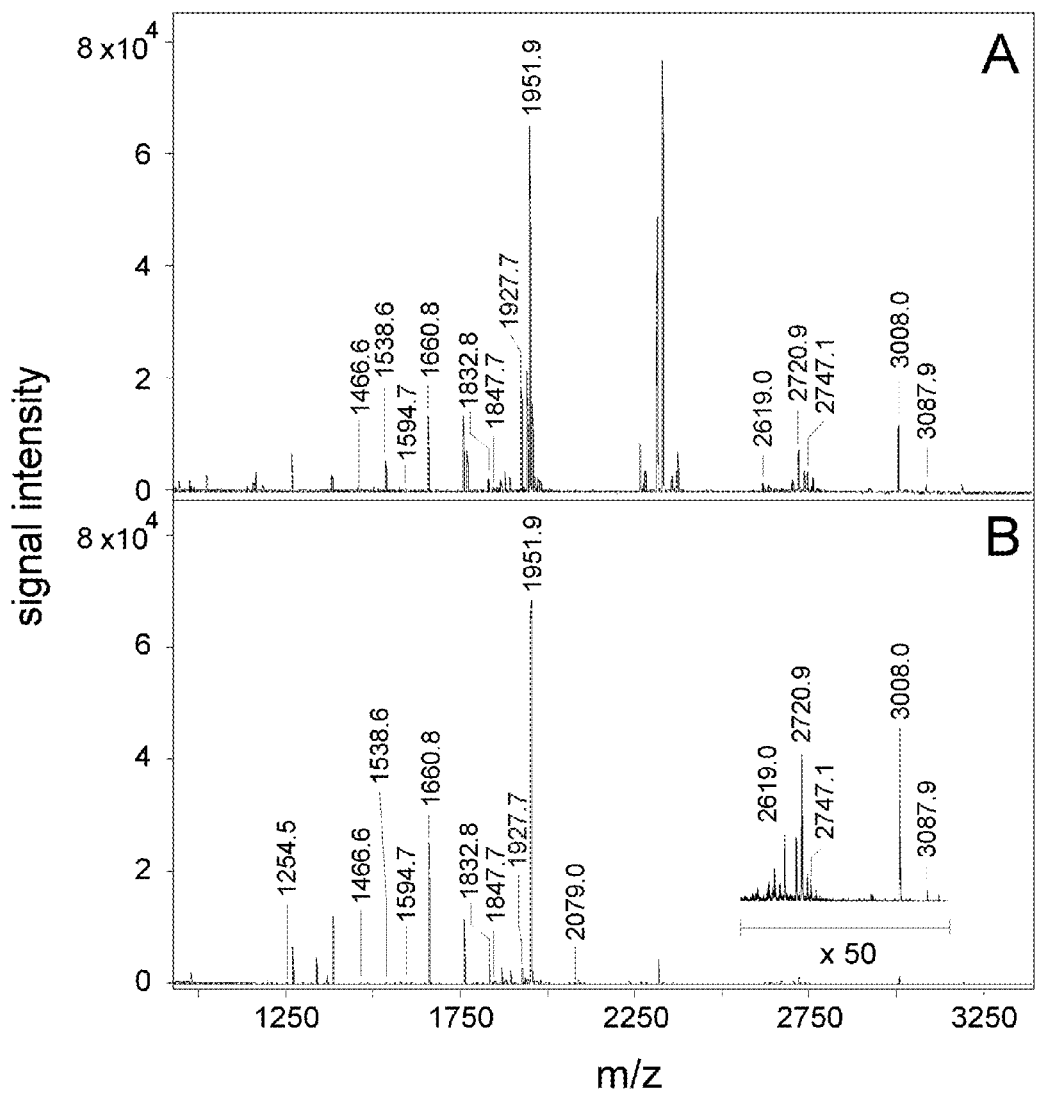
FIG. 3 MALDI-MS spectra, obtained after specific enrichment of (A) α-casein digest with poly(DVB)-$TiO_2$ extraction tips and (B) mixed poly(DVB)-$TiO_2/ZrO_2$ tips.

In case of mixed $ZrO_2/TiO_2$ tips all five phosphopeptides resulting from tryptic digestion could be retained from the β-casein digest (FIG. 2B) and twenty phosphopeptides from α-casein digest (FIG. 3B). All labelled signals corresponded to phosphorylated peptides and their fragment ions. One extra phosphopeptide at m/z 2432.1 was exclusively retained on the mixed phase (FIG. 3B).

TABLE 3

| Monoisotopic Mass [M + H]+ Da | Number of phosphate groups | Poly(DVB)-TiO2/ZrO2 S/N | Poly(DVB)-TiO2 S/N | ZipTipMC Fe3+ S/N | MonoTip TiO2 S/N | TopTip-TiO2 S/N | TopTip-ZrO2 S/N |
|---|---|---|---|---|---|---|---|
| 2061.82 | 1 | 1683.9 | 589.1 | 83.5 | 1268.9 | 768.5 | 42.1 |
| 2432.05 | 1 | 22.3 | — | — | 27.4 | — | — |
| 2966.16 | 4 | 9.0 | 14.1 | — | 11.3 | — | — |
| 3042.50 | 3 | 23.4 | 51.0 | — | 40.6 | — | — |
| 3122.27 | 4 | 200.7 | 189.5 | 12.8 | 239.4 | 15.1 | — |
| Number of phosphate groups detected | | 5 | 4 | 2 | 5 | 2 | 1 |

The fabricated $TiO_2/ZrO_2$ embedded extraction tips were compared to commercial phosphorylation-enrichment kits including ZipTip® MC-$Fe^{3+}$ (Millipore), TopTips (Glygen Corp.) and MonoTips (GL Sciences Inc.) and superior selectivities for binding phosphopeptides were observed by applying self-fabricated. The total number of recovered phosphopeptides for β-casein and α-casein digests including their corresponding signal-to-noise (S/N) ratios are listed in Table 4.

ments of two synthetic phosphopeptides (DpSEGRGpSGD-PGK [M+H]+=1321.45 Da, and VYGKTpSHLR [M+H]+=1140.56 Da). Mixed poly(DVB)-$TiO_2/ZrO_2$ tips were incubated each time with 10 μL of different concentrated phosphopeptide standards. The lowest detectable amount of phosphopeptide was estimated at the low femtomole level (~5 to 10 fmol/μl).

TABLE 4

| Monoisotopic Mass [M + H]+ Da | Number of phosphate groups | Poly(DVB)-TiO2/ZrO2 S/N | Poly(DVB)-TiO2 S/N | ZipTipMC Fe3+ S/N | MonoTip TiO2 S/N | TopTip-TiO2 S/N | TopTip-ZrO2 S/N |
|---|---|---|---|---|---|---|---|
| 1254.52[a] | 1 | 18.2 | — | — | — | 10.3 | 61.0 |
| 1331.53 | 1 | — | — | — | — | — | — |
| 1411.50 | 2 | — | — | — | — | — | — |
| 1466.99 | 1 | 28.9 | 5.0 | — | 17.2 | 15.5 | — |
| 1482.69[b] | 1 | 15.5 | — | — | 7.9 | — | — |
| 1538.59 | 2 | 22.2 | 36.4 | — | — | — | — |
| 1594.70 | 1 | 23.3 | 5.3 | — | 35.6 | 19.0 | 17.9 |
| 1660.79 | 1 | 2459.7 | 86.5 | 35.0 | 229.6 | 672.4 | 599.6 |
| 1832.83 | 1 | 334.5 | 16.0 | 14.5 | 35.6 | 68.4 | 31.5 |
| 1847.69 | 1 | 48.4 | 6.4 | — | 20.9 | 12.4 | 7.9 |
| 1927.69 | 2 | 268.0 | 117.8 | 27.1 | 72.1 | 70.3 | — |
| 1943.79[b] | 2 | 87.3 | 137.9 | 26.9 | 26.5 | 21.0 | 8.3 |
| 1951.95 | 1 | 6380.6 | 354.5 | 145.1 | 745.5 | 2382.6 | 1208.6 |
| 2079.04 | 1 | 23.5 | — | — | 8.7 | 7.7 | 9.0 |
| 2619.04 | 4 | 9.1 | 7.2 | — | — | — | — |
| 2678.01 | 3 | 5.4 | — | — | — | — | — |
| 2720.91 | 5 | 114.9 | 35.6 | — | — | — | — |
| 2737.91[b] | 5 | 14.2 | 15.9 | — | — | — | — |
| 2747.10 | 4 | 10.8 | 24.1 | — | — | — | — |
| 2935.15 | 3 | — | — | — | — | — | — |
| 3008.01 | 4 | 76.2 | 51.0 | 155.2 | — | — | — |
| 3087.99 | 5 | 7.5 | 6.4 | 10.3 | — | — | — |
| 3132.20 | 4 | — | — | — | — | — | — |
| 4717.93 | 4 | 31.7 | 45.6 | — | 5.0 | 16.9 | 72.1 |
| Number of phosphate groups detected | | 20 | 16 | 7 | 11 | 11 | 9 |

[a]unusual cleavage (ovalbumin)
[b]oxidized methionine and phosphoserine

Example 7

Detection of Femtomolar Amounts of Phosphopeptides

The ability to detect sub-picomolar amounts of phosphorylated peptides was carried out by MALDI-MS measure- Example 8

Analysis of In Vitro Phosphorylation of ERK-1 by MEK-2

Figure 4:
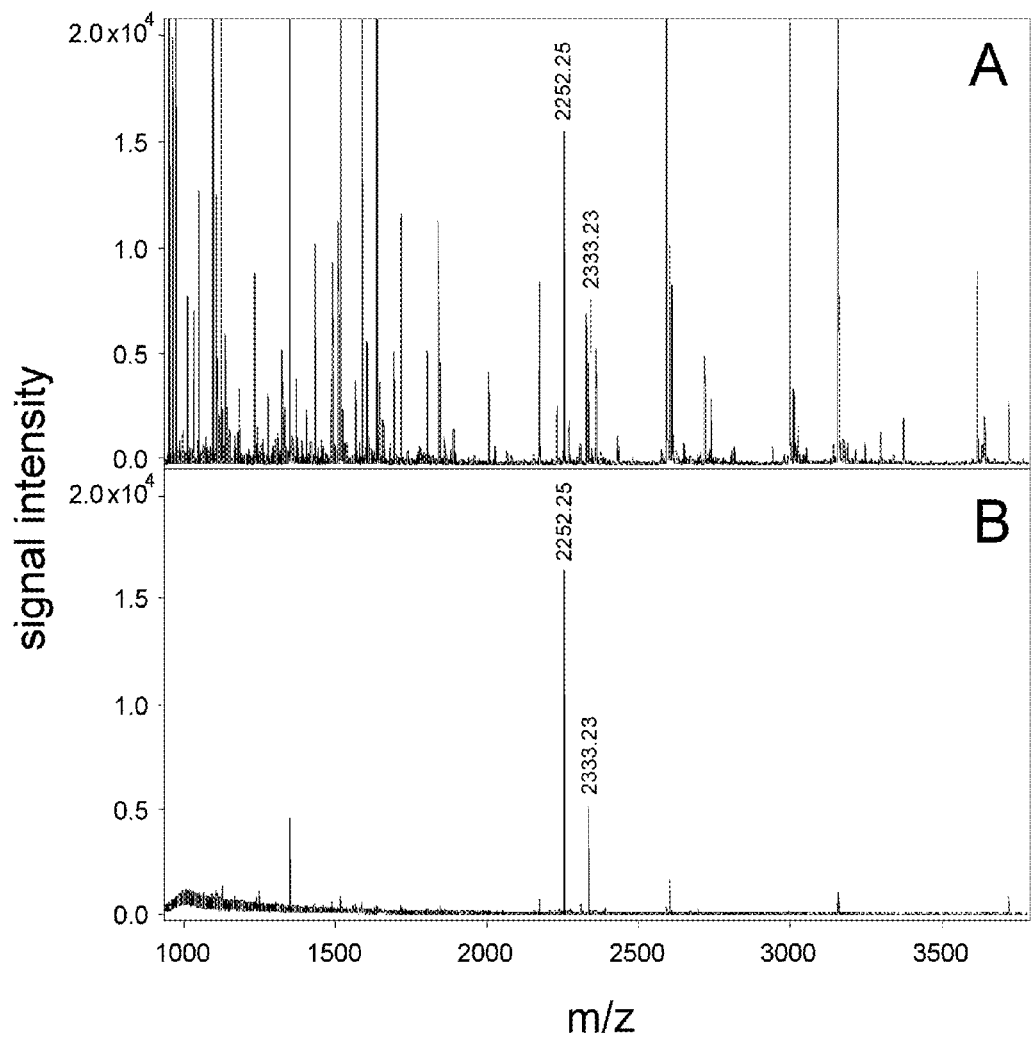
FIG. 4 is the MALDI mass spectrum obtained from in vitro phosphorylated ERK1 digest (A) before (B) and after enrichment with poly(DVB)-$TiO_2/ZrO_2$ micro columns.

The ERK cascade regulates distinct processes such as proliferation, cell migration and survival in multi-cellular organisms. Mammalian cells contain three members of the RAF family, two different MEK proteins, and two ERK proteins. MEK-2 is a member of a tyrosine/threonine protein kinase family that activates ERK1&2/MAPK enzymes by phosphorylating both residues within threonine-glutamic acid-tyrosine (TEY) motif. MEK-2 typically phosphorylates ERK1 at Thr-202 and Tyr-204. ERK1 was phosphorylated by MEK-2 as described in materials and methods, and subjected to tryptic digestion.

in vitro phosphorylation of extracellular signal-regulated kinase 1 (ERK-1) by MEK-2, a mitogen-activated protein kinase (MAPK) was performed and the results were analyzed using MALDI/TOF-MS. FIG. 4A shows the mass spectrum obtained from in vitro phosphorylated ERK1 digest before enrichments with a poly(DVB)-$TiO_2$/$ZrO_2$ micro column. After enrichment of peptides with poly(DVB)-$TiO_2$/$ZrO_2$ extraction tips, two phosphorylated peptides (m/z 2252.25 and 2332.23) could be detected by MALDI/TOF-MS analysis as demonstrated in FIG. 4B. The signal-to-noise (S/N) ratios of the two phosphopeptide ion signals were significantly improved to those obtained from the original peptide mixture demonstrating the importance of reducing the complexity of the peptide mixture and increasing the relative amount of phosphopeptides.

Figure 6:
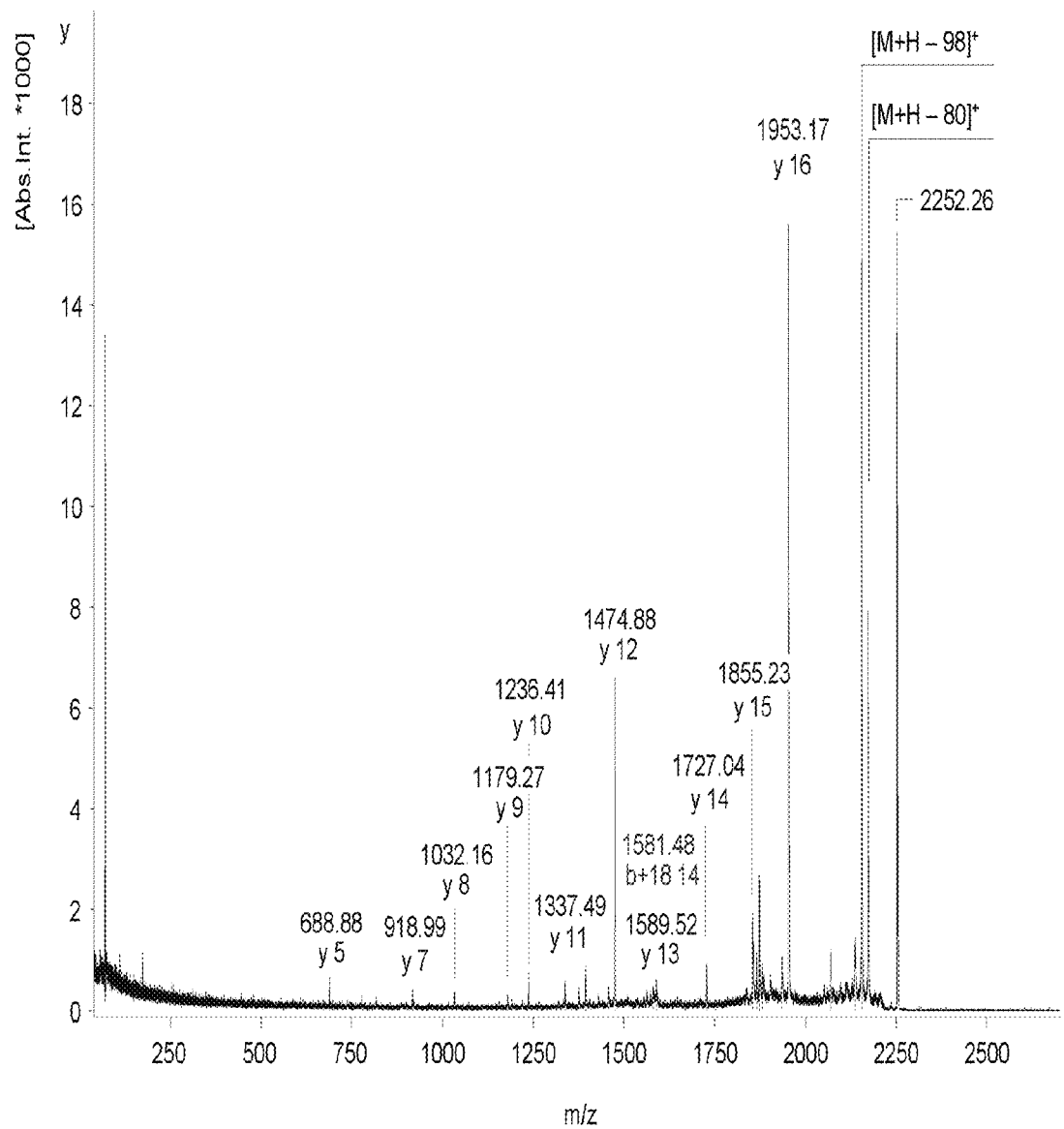
FIG. 6 shows a MALDI-TOT/TOF mass spectrum of mono-phosphorylated peptide (m/z 2252.25) acquired from tryptic digest of ERK1 after isolation by poly(DVB)-$TiO_2/ZrO_2$ tips.
Figure 7:
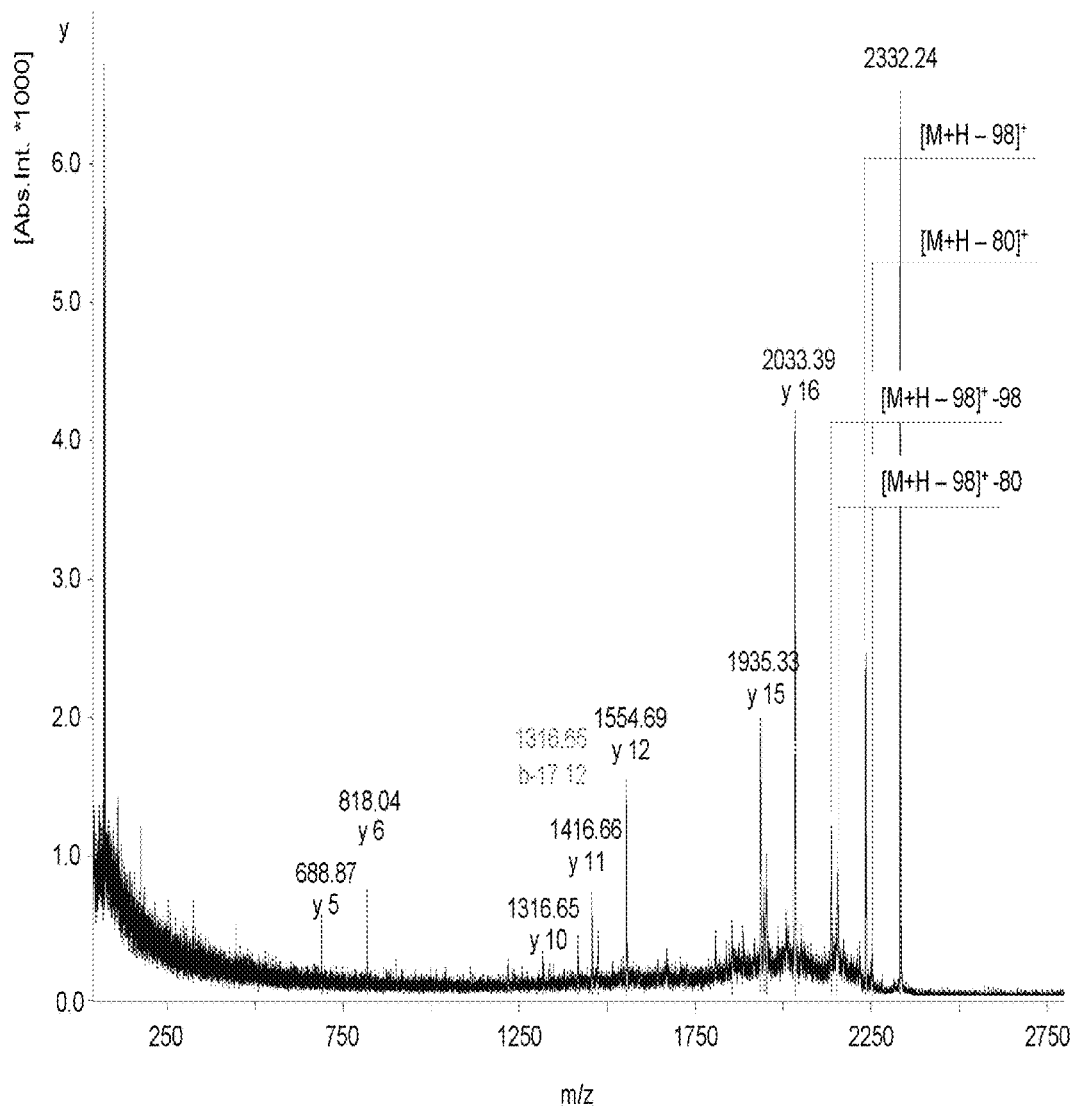
FIG. 7 shows a MALDI mass spectrum of m/z 2332.23 corresponds to MS/MS fragmentation of RIADPEHDHTG-FLpTEpYVATRW acquired from tryptic digest of ERK1 after enrichment by poly(DVB)-$TiO_2/ZrO_2$ tips and SwissProt database searching.

Tandem MS analysis of the phosphopeptide at m/z 2252.25 $[M+H]^+$ resulted in the detection of the loss of $H_3PO_4$ $[M+H -98]^+$ and the loss of $HPO_3$ $[M+H -80]^+$. A subsequent database searching analysis with Mascot software revealed the following sequence RIADPEHDHTGFLTEpYVATRW. Further MALDI-TOF/TOF measurements of the second phosphorylated peptide at m/z 2332.23 $[M+H]^+$ showed apparent losses of two phosphoric acid groups from the precursor ion (successive losses of 98 Da from the precursor ion) (FIG. 6). The MALDI spectrum of m/z 2332.23 corresponds to MS/MS fragmentation of RIADPEHDHTGFLpTEpYVATRW (FIG. 7). The fragment ions indicate that the peptide is most likely phosphorylated at threonine and tyrosine.

Example 9

$In_2O_3$— and $MnO_2$ Tips for Phosphopeptide Enrichment

For the polymerization of $In_2O_3$ and $MnO_2$ doped poly (DVB) pipette tips, a polymerization mixture comprising DVB (150 μL; free of inhibitors), distilled decanol (150 μL), anhydrous toluene (100 μL) and AIBN (10 mg) is prepared. 200 μL of the polymerization mixture is added to a glass vial containing either 50 mg of $In_2O_3$ or 55 mg of $MnO_2$ nanopowders (<100 nm). The mixtures are vortexed and ultra-sonicated at room temperature to form the stable pre-monolith suspension. Two microliters of the suspended polymerization mixtures are aspirated into 10 μl pipette tips (Rainin). The structure formed against the wall of the tip remains. The tips are placed into an oven for 2.5 hours at 80° C. Alternatively, the tips are polymerized with UV light or radiation. After polymerization, the extraction tips are extensively washed with ACN and MeOH to remove all unreacted components.

Example 10

Monolithic C60 Extraction Tips for Desalting

For the preparation of C60-embedded monolithic pipette tips, a polymerization mixture comprising a C60-fullerene saturated DVB solution (100 μL), distilled decanol (100 μL) and AIBN (10 mg) is prepared. The mixture is vortexed and ultra-sonicated at room temperature to create the pre-monolith suspension. One to three microliters of the suspended polymerization mixture is aspirated into 10 μl pipette tips (Rainin). Next, the tips are placed into a heating chamber at 80° C. for 2.5 hours. After the polymerization process, the pipette tips are extensively washed with ACN and MeOH to remove all unreacted components.

Example 11

Preparation of Monolithic Diamond-Embedded SPE Tips for Desalting

A polymerization mixture containing distilled GMA (150 μL), DVB (150 μL; free of inhibitors), distilled decanol (150 μL) and AIBN (20 mg) is prepared. Then, 200 μL of the polymerization mixture is added to a glass vial containing 20 mg of diamond nanopowder (~10 nm). Furthermore anhydrous toluene (50 μL) is added. The mixture is vortexed and ultra-sonicated at room temperature to create the pre-monolith suspension. One to three microliters of the suspension are aspirated into 10 μL pipette tips (Rainin). The center portion of the suspension is expelled. Next, the tips are placed into a heating chamber at 80° C. for 2.5 hours. After polymerization process, the pipette tips are extensively washed with ACN and MeOH to remove all unreacted components.

Example 12

DEAE (Diethylaminoethyl) on C60 for Enriching Anions

The oxidation of C60-fullerene is carried out using a tenfold molar excess of m-chloroperoxybenzoic acid, which is purified by washing it with a PBS buffer (pH 7.4). M-chloroperoxybenzoic acid is added to a preheated solution (80° C.) of fullerenes (300 mg, 0.416 mmol) dissolved in 150 ml toluene. After 12 h, the toluene is evaporated and the resulting brown solid is thoroughly washed with methanol to remove the excess of m-chloroperoxybenzoic acid and dried under vacuum. The resulting epoxy-fullerenes are then dissolved in 150 ml toluene and a 3-fold molar excess of DEAE is added. The mixture is stirred under inert conditions at 80° C. for 12 h. Finally, toluene is evaporated and the residue is thoroughly washed to remove all unreacted compounds.

Example 13

Hollow Monolith (PhyTip Tizr) Column Manufacturing Protocol

A) Remove Inhibitor from DVB:
1) Add 20 mL volume of inhibitor removal (Sigma 9003-70-7) into glass column.
2) Measure out 25 mL of DVB (EMD D42403-2) and pour over the glass column.
3) Collect first 5 mL and discard.
4) Collect 20 mL and keep in the fridge for future use (only good for 2 weeks).
B) Making Solution Mix:
1) Add 300 uL of DVB from step A.
2) Add 300 uL of 1-Decanol (Sigma 239763-50G).
3) Add 200 uL of Toluene (Fluka 89681).
4) Add 22 mg AIBN (Aldrich 441090-25G), use 2 mL tubes.
   Total volume=800 uL
5) Sonicate for 5 minutes until AIBN is in solution.

C) Addition of Ti/Zr:
1) To above 800 uL, add 140 mg TiO2 (Sigma 637254-50G).
2) Add 140 mg ZrO2 (Sigma 544760-5G).
3) Sonicate 10 minutes, vortex, sonicate for another 5 minutes.
D) Pipette Manipulation & Heating:
1) Aliquot 60 uL of slurry to each tube in 12 strip PCR tubes (total 720 uL).
2) Intake 0.8 uL and expel the liquid onto a paper towel using 12 channel 10 uL electronic pipette (Slurry should stick to the inside of the tip). Use speed 1.
3) Eject the tip into the tip box.
4) Put tip box (no cover) in 80 C for 2.5 hrs.
E) Final Wash:
1) Set up two reservoirs. One with acetone and other with 100% alcohol'
2) Using above monolith tips, intake and expel 1 uL of acetone (pipette speed 1) twice.
3) Intake and expel 1 uL of 100% alcohol twice and eject them back into the tip box.
4) Move the box with tips into the oven for 1 hour at 42 C (no cover).
F) Packaging:
1) Attach quick start guide to the top of the cover using double sided tape.
2) Print attaché box label and shrink wrap.
3) Place insert sheet in the box.

What is claimed is:

1. A method of preparing a hollow monolith in a pipette tip comprising the steps of:
    a. preparing a stable, pre-monolith suspension comprised of monomers, porogens, particles and optionally, an initiator and a crosslinker;
    b. introducing the stable, pre-monolith suspension into a pipette tip;
    c. removing the center portion of the stable, pre-monolith suspension; and
    d. polymerizing the stable, pre-monolith suspension to form a stable hollow monolith structure inside the pipette tip.

2. The method of claim 1, wherein the pipette tip attached to a pipette, wherein step (b) is performed by aspirating the stable, pre-monolith suspension through the lower end of the pipette tip, and wherein step (c) is performed by expelling a portion of the stable, pre-monolith suspension through the lower end of the pipette tip.

3. The method of claim 1, wherein said particles are selected from the group consisting of silica, metal oxides, metals, ceramics, synthetic polymers, biopolymers, and allotropes of carbon.

4. The method of claim 3, wherein the allotropes of carbon are selected from the group consisting of fullerenes, diamond, graphite, nanotubes and nanowires.

5. The method of claim 1, wherein said particles are mixtures selected from the group consisting of silica, metal oxides, metals, ceramics, synthetic polymers, biopolymers and allotropes of carbon.

6. The method of claim 1, wherein the size of said particles is in the range of 1 nanometer to 100 micrometers.

7. The method of claim 6, wherein the size of the particles is in the range of 20 nanometers to 5 micrometers.

8. The method of claim 7, wherein the size of the particles is in the range of 100 nanometers to 2 micrometers.

9. The method of claim 1, wherein the chemical group is a comprised of an affinity group.

10. An automated method of preparing a plurality of pipette tips containing a hollow monolith comprising the steps of:
    a. providing a liquid handling system, wherein the system is operatively engaged with a plurality of pipette tips;
    b. aspirating a stable, pre-monolith suspension into the pipette tips; and
    c. expelling a portion of the stable, pre-monolith suspension.

* * * * *